US007208072B2

(12) United States Patent
Amirkhanian et al.

(10) Patent No.: US 7,208,072 B2
(45) Date of Patent: *Apr. 24, 2007

(54) MULTI-SEGMENT CARTRIDGE FOR BIO-SEPARATION WITH MULTIPLEXED FLUORESCENCE DETECTION

(75) Inventors: Varouj Amirkhanian, La Crescenta, CA (US); Ming-Sun Liu, Brea, CA (US); Paul Mooney, Rancho Santa Margarita, CA (US)

(73) Assignee: Biocal Technology, Inc., Irvine, CA (US)

( * ) Notice: Subject to any disclaimer, the term of this patent is extended or adjusted under 35 U.S.C. 154(b) by 382 days.

This patent is subject to a terminal disclaimer.

(21) Appl. No.: 10/349,316

(22) Filed: Jan. 21, 2003

(65) Prior Publication Data

US 2003/0178312 A1 Sep. 25, 2003

Related U.S. Application Data

(63) Continuation-in-part of application No. 10/059,993, filed on Jan. 28, 2002.

(60) Provisional application No. 60/349,904, filed on Jan. 18, 2002.

(51) Int. Cl.
*G01N 27/26* (2006.01)
(52) U.S. Cl. ...................... 204/603; 204/605; 204/616; 204/612
(58) Field of Classification Search ................ 204/450, 204/451, 452, 453, 455, 456, 461, 546, 600, 204/601, 603, 604, 605, 606, 612, 641
See application file for complete search history.

(56) References Cited

U.S. PATENT DOCUMENTS 4,417,967 A 11/1983 Ledley (Continued)

FOREIGN PATENT DOCUMENTS

EP 0021499 1/1981

(Continued)

OTHER PUBLICATIONS

Quesada, M.A., and Zhang, S., "Multiple capillary DNA sequencer that uses fiber-optic illumination and detection", Electrophoresis, 17, 1996, pp. 1841-1851.*

(Continued)

*Primary Examiner*—Nam Nguyen
*Assistant Examiner*—Anthony Fick
(74) *Attorney, Agent, or Firm*—Liu & Liu

(57) ABSTRACT

A bio-separation instrument using a multi-segment cartridge. The cartridge includes a plurality of efficient, compact, portable, interchangeable, reusable, recyclable, modular, multi-channel segments. Each segment supports multiple capillaries for CE separation. Each segment has an integrated reservoir containing a buffer/gel common to all the capillaries. Air pressure can be supplied to the reservoir through the periphery of each segment. Each segment has an integrated LED array board directly coupled to capillaries for providing excitation light. Optical fibers of a fiber bundle are individually guided through the periphery of each segment to the capillaries for emission collection. The fiber bundle delivers emissions to a detector that can read the emissions in a time-staggered multiplexed scheme. Each segment includes electrodes electrically coupled to a voltage source through the periphery of the segment for effecting CE separation. Providing each segment with pneumatic and voltage connections on the periphery and direct coupling LED's allow the segments to easily stack together for integration into the instrument.

24 Claims, 12 Drawing Sheets

U.S. PATENT DOCUMENTS

| | | | |
|---|---|---|---|
| 4,675,300 A * | 6/1987 | Zare et al. | 204/452 |
| 4,827,780 A | 5/1989 | Sarrine et al. | |
| 5,062,942 A | 11/1991 | Kambara et al. | |
| 5,066,382 A | 11/1991 | Weinberger et al. | |
| 5,192,412 A | 3/1993 | Kambara et al. | |
| 5,198,091 A | 3/1993 | Burolla et al. | |
| 5,324,401 A | 6/1994 | Yeung et al. | |
| 5,338,427 A | 8/1994 | Shartle et al. | |
| 5,366,608 A | 11/1994 | Kambara | |
| 5,413,686 A | 5/1995 | Klein et al. | |
| 5,416,879 A | 5/1995 | Liu | |
| 5,439,578 A | 8/1995 | Dovichi et al. | |
| 5,498,324 A | 3/1996 | Yeung et al. | |
| 5,529,679 A | 6/1996 | Takahashi et al. | |
| 5,543,018 A | 8/1996 | Stevens et al. | |
| 5,560,811 A * | 10/1996 | Briggs et al. | 204/451 |
| 5,584,982 A | 12/1996 | Dovichi et al. | |
| 5,625,403 A | 4/1997 | Hazman et al. | |
| 5,635,050 A | 6/1997 | Pentoney et al. | |
| 5,650,846 A | 7/1997 | Yin et al. | |
| 5,675,155 A | 10/1997 | Pentoney, Jr. et al. | |
| 5,741,411 A | 4/1998 | Yeung et al. | |
| 5,741,412 A | 4/1998 | Dovichi et al. | |
| 5,763,277 A | 6/1998 | Zhu et al. | |
| 5,790,727 A | 8/1998 | Dhadwal et al. | |
| 5,846,727 A | 12/1998 | Soper et al. | |
| 5,865,974 A | 2/1999 | Cabilly et al. | |
| 5,916,428 A | 6/1999 | Kane et al. | |
| 5,968,331 A | 10/1999 | Kambara et al. | |
| 6,001,230 A | 12/1999 | Burolla | |
| 6,013,165 A | 1/2000 | Wiktorowicz et al. | |
| 6,017,765 A | 1/2000 | Yamada et al. | |
| 6,027,627 A | 2/2000 | Li et al. | |
| 6,043,880 A | 3/2000 | Andrews et al. | |
| 6,054,032 A | 4/2000 | Haddad et al. | |
| 6,063,251 A | 5/2000 | Kane et al. | |
| 6,074,827 A | 6/2000 | Nelson et al. | |
| 6,084,667 A * | 7/2000 | Melman et al. | 356/246 |
| 6,103,083 A | 8/2000 | Merenkova et al. | |
| 6,104,485 A | 8/2000 | Wang et al. | |
| 6,132,578 A | 10/2000 | Kambara et al. | |
| 6,153,437 A | 11/2000 | Horn | |
| 6,184,990 B1 | 2/2001 | Amirkhanian et al. | |
| 6,326,213 B1 | 12/2001 | Letcher et al. | |
| RE37,606 E | 3/2002 | Guttman | |
| 6,369,893 B1 | 4/2002 | Christel et al. | |
| 6,375,819 B1 | 4/2002 | Li et al. | |
| 6,445,448 B1 | 9/2002 | Melman et al. | |
| RE37,941 E | 12/2002 | Guttman | |
| 6,595,979 B1 * | 7/2003 | Epstein et al. | 604/506 |
| 6,752,914 B1 | 6/2004 | Hassard | |
| 6,828,567 B2 | 12/2004 | Amirkhanian et al. | |
| 6,870,165 B2 | 3/2005 | Amirkhanian et al. | |
| 6,974,528 B2 | 12/2005 | Liu et al. | |
| 2002/0092770 A1 | 7/2002 | Hedberg et al. | |

FOREIGN PATENT DOCUMENTS

| | | |
|---|---|---|
| EP | 0631134 A2 | 12/1994 |
| EP | 0723149 | 7/1996 |
| JP | 10-206384 | 8/1998 |
| JP | 11023533 | 1/1999 |
| JP | 11230938 | 8/1999 |
| JP | 2001-124736 | 5/2001 |
| WO | WO98/10122 | 3/1998 |
| WO | WO00/006996 | 2/2000 |
| WO | WO01/02846 | 1/2001 |
| WO | WO 02/28509 | 4/2002 |
| WO | WO 02/059589 | 8/2002 |

OTHER PUBLICATIONS

"Laser-Induced Fluorescence Detection of a Single Molecule in a Capillary", by Lee, et al., Analytical Chemistry, vol. 66, No. 23, Dec. 1, 1994, pp. 4142-4149.

"Up to Speed on PCR", by Deborah A. Fitzgerald, The Scientist, Nov. 27, 2000, pp. 31-33.

"Low-Cost, High-Sensitivity Laser-Induced Fluorescence Detection for DNA Sequencing by Capillary Gel Electrophoresis", Chen, et al., Journal of Chromatography, vol. 559, 1991, pp. 237-246.

"Multiple Capillary DNA Sequencer that Uses Fiber-Optic Illumination and Detection", by Quesada, et al., Electrophoresis, vol. 17, 1996, pp. 1841-1851.

"Axial-Beam Laser-Excited Fluorescence Detection in Capillary Electrophoresis" by Taylor, et al., Analytical Chemistry, vol. 64, No. 15, Aug. 1, 1992, pp. 1741-1744.

"Multiplexed Fluorescence Detector for Capillary Electrophoresis Using Axial Optical Fiber Illumination", by Taylor, et al., Analytical Chemistry, vol. 65, No. 7, Apr. 1, 1993, pp. 956-960.

International Search Report of Counterpart PCT Application No. PCT/US02/02515, Feb. 11, 2003.

International Search Report of Counterpart PCT Application No. PCT/US03/01841, Jul. 7, 2003.

International Search Report of Counterpart PCT Application No. PCT/US02/02514, Oct. 18, 2002.

"Using cIEF to Characterize Recombinant Human Monoclonal Antibodies", Pace Setter, vol. 3, Issue 1, Apr. 1999.

"Simultaneous Monitoring of DNA Fragments Separated by Electrophoresis in a Multiplexed Array of 100 Capillaries", by Ueno, et al., Analytical Chemistry, vol. 66, No. 9, May 1, 1994, pp. 1424-1431.

"DNA Analysis Tools Shrink", by Richard Gaughan, Biophotonics International, Jul./Aug. 2000, pp. 18-19.

"An Integrated Nanoliter DNA Analysis Device", by Burns, et al., Science, vol. 282, Oct. 16, 1998, pp. 484-487.

"DNA Sequencing Using Capillary Array Electrophoresis", by Huang, et al., Analytical Chemistry, vol. 64, No. 18, Sep. 15, 1992, pp. 2149-2154.

"Three DNA Sequencing Methods Using Capillary Gel Electrophoresis and Laser-Induced Fluorescence", by Swerdlow, et al., Analytical Chemistry, vol. 63, No. 24, Dec. 15, 1991, pp. 2835-2841.

"DNA Sequencing by Multiple Capillaries that Form a Waveguide", by Dhadwal, et al., pp. 1-14, date not available.

"A Capillary Array Gel Electrophoresis System Using Multiple Laser Focusing for DNA Sequencing", by Anazawa, et al., Analytical Chemistry, vol. 68, No. 15, Aug. 1, 1996, pp. 2699-2704.

"Researchers Design DNA Lab on a Chip", by Kate Leggett, Biophotonics International, Jan./Feb. 1999.

Taylor, et al, "Axial-Beam Laser-Excited Fluorescence Detection in Capillary Electrophoresis", Anal. Chem., (1992) vol. 64, pp. 1741-1744.

Taylor, et al, "Multiplexed Fluorescence Detector for Capillary Electrophoresis Using Axial Optical Fiber Illumination", Anal. Chem., (1993) vol. 65, pp. 956-960.

Ueno, et al., "Simultaneous Monitoring of DNA Fragments Separated by Electrophoresis in a Multiplexed Array of 100 Capillaries", Anal. Chem. (1994) vol. 66, No. 9, pp. 1424-1431.

International Search Report of Counterpart PCT Application No. PCT/US2004/043424, Aug. 10, 2005.

International Search Report of Counterpart PCT Application No. PCT/US2004/011376, Sep. 2, 2004.

* cited by examiner

MULTI-SEGMENT CARTRIDGE FOR BIO-SEPARATION WITH MULTIPLEXED FLUORESCENCE DETECTION

This application claims the priority of U.S. Provisional Patent Application No. 60/349,904, filed on Jan. 18, 2002.

This application is a Continuation-in-Part of U.S. patent application Ser. No. 10/059,993, entitled "Multi-Channel Bio-Separation Cartridge," filed on Jan. 28, 2002, which is commonly assigned to BioCal Technology, Inc., the assignee of the present invention, and which is fully incorporated by reference herein.

BACKGROUND OF THE INVENTION

The present invention relates to bio-separation, and more particularly to a multi-segment cartridge for supporting multi-separation columns with integrated reagent reservoir and excitation radiation and a bio-separation instrument incorporating the cartridge.

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to ease sample handling during the process, and in general, to have a simplified, low cost, high sensitivity detector.

One type of DNA analysis instrument separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a multi-lane slab gel electrophoresis instrument, which as the name suggests, uses a slab of gel on which DNA samples are placed. Electric charges are applied across the gel slab, which cause the DNA sample to be separated into DNA fragments of different masses.

Another type of electrophoresis instrument is the capillary electrophoresis (CE) instrument. By applying electrophoresis in a fused silica capillary column carrying a buffer solution, the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample. In the past, Laser-induced fluorescence (LIF) detection methods had been developed for CE instruments. Fluorescence detection is often the detection method of choice in the fields of genomics and proteomics because of its outstanding sensitivity compared to other detection methods.

Some of the challenges in designing CE-based instruments and CE analysis protocols relates to sample detection techniques. In the case of fluorescence detection, considerable design considerations had been given to, for example, radiation source, optical detection, sensitivity and reliability of the detection, cost and reliability of the structure of the detection optics. In the past, a relatively high power light source is required, such as a Laser. When light is directed through the capillary wall at the separated sample components in the capillary bore, light scatters at the outside capillary wall/air interface and the inside capillary wall/buffer interface (Raman scattering), which obscures or corrupts the fluorescence emission intensity. Similarly, fluorescence emissions scatter at the wall interfaces. In the past, various techniques were developed for more completely collecting the fluorescence emissions to improve signal intensity and hence detection sensitivity. These techniques involve additional moving and non-moving components that add to the relative complexity and cost of the detection setup.

The design limitations of prior art electrophoresis instruments are exacerbated in the development of multi-capillary CE-based instruments. For example, confocal scanning laser induced fluorescence (LIF) detection has been adopted in multi-capillary electrophoresis systems. The scanning confocal detection relies on a scanning optical system. The use of moving parts is not ideal when taking simplicity, robustness, and lower cost of the instrument into consideration. Also, the shallow focal depth of the microscope objective for the confocal detector puts severe demands on the mechanical and optical component tolerances. Further, the optical scanning method generally involves a longer duty cycle per capillary. Thus, should the instrument be scaled up in order to generate higher throughput, the sensitivity of the system may be compromised. Also, another detection method is Sheath Flow detection. The main drawback of the sheath flow detector is the highly sophisticated flow system needed to ensure a reliable sheath flow with minimum optical cross talk between the channels. Extreme demands are put on the optical and mechanical component tolerances in order to meet the robustness demands of end-users. The sensitivity of the device is very good, but it is not obvious that this principle of fluorescence detection is suited for a high-throughput, yet low cost, DNA analysis.

Additional challenges in designing multi-capillary CE-based instruments relate to the support of the capillaries. U.S. Pat. No. 5,198,091 to Burolla et al. describes a capillary cartridge for electrophoresis that employs a long length of capillary arrays. This patent may include a hollow space defined about the capillary for circulating coolant fluid but it does not include a reservoir as an integrated part of the cartridge. U.S. Pat. No. 5,413,686 to Klein et al. describes an automated multi-channel capillary electrophoresis analyzer including a plurality of capillaries. Reservoirs are shown in the analyzing apparatus, but they are multiple reservoirs and they are separated from the capillaries, not integrated into a capillary support. Detection optics are also shown in the apparatus, but they are not integrated into a compact capillary support. U.S. Pat. No. 5,338,427 to Shartle et al. describes a single use separation cartridge for a capillary electrophoresis instrument, in which capillary tubes are horizontally disposed in a coplanar array. The single use separation cartridge replaces large reagent reservoirs with hemispherical drops of reagent.

Also, current systems for gel buffer chemistry do not allow use of the CE instrument that is specific with applications. In other words, current CE instruments require matching the capillary (with different coatings and column sizes) with the buffer reagent for different separation applications (different types, speeds, resolutions).

SUMMARY OF THE INVENTION

The present invention provides for a bio-separation instrument that uses a multi-segment cartridge. The cartridge includes a plurality of efficient, compact, portable, interchangeable, reusable, recyclable, modular, multi-channel segments stacked together. In one aspect of the present invention, the instrument uses a cartridge having one or more modular segments stacked together. Each segment supports multiple capillaries. The stacked segments support a capillary grid for parallel CE separation.

In another aspect of the present invention, each segment of the cartridge has an integrated reservoir holding a buffer/gel common to all the capillaries. The reservoir of each segment is connectable to an air pressure pump through the periphery of each segment. By providing connection on the periphery, the air pressure connection does not interfere with the segments stacking with each other.

In another aspect of the present invention, each segment has an integrated LED array board directly coupled to the capillaries for providing excitation light. The LED array board provides an efficient, compact and interchangeable means for integrating the radiation source to the cartridge without interfering with the segments stacking with each other.

In another aspect of the present invention, optical fibers of a fiber bundle are individually guided through the periphery of each segment to the capillaries for emission collection. The routing the fibers through the periphery of each segment, the fibers do not interfere with the segments stacking with each other. The fiber bundle delivers emissions to a detector that can read the emissions in a time-staggered multiplexed scheme.

In a further aspect of the present invention, each segment includes electrodes electrically coupled to a voltage source through the periphery of the segment for effecting CE separation. Electrical connections on the periphery allow the segments to stack together without interference.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed to a novel CE instrument and novel multi-segment cartridge. For purpose of illustrating the principles of the present invention and not by limitation, the present invention is described by reference to embodiments directed to capillary electrophoresis and radiation induced fluorescence.

Figure 1:
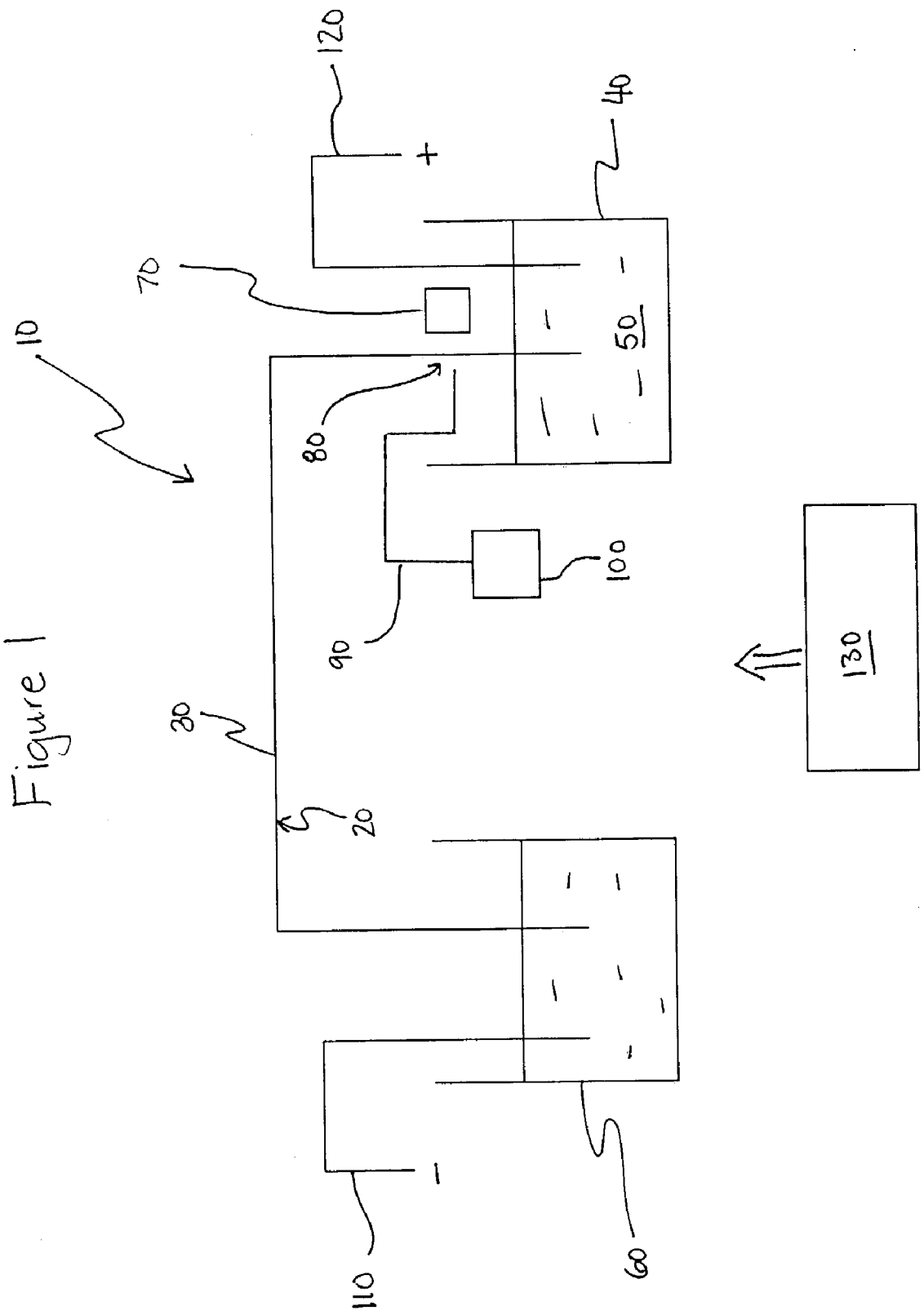
FIG. 1 is a schematic view of a capillary electrophoresis system that incorporates the present invention.

FIG. 1 is a schematic diagram illustrating a bio-separation system, more specifically a capillary electrophoresis (CE) system 10, which incorporates the present invention. The CE system 10 generally comprises a capillary separation column 20 (e.g., 200–500 μm O.D.), which defines a separation channel 30 (e.g., 25–200 μm I.D.). The capillary column 30 may be made of fused silica, glass, polyimide, or other plastic/ceramic/glassy materials. The inside walls of the separation column 20 (i.e., the walls of the separation channel 30) may be coated with a material that can build up an electrostatic charge to facilitate electrophoresis and/or electrokinetic migration of the sample components. The separation channel 30 is filled with a separation support medium, which may simply be a running buffer, or a sieving gel matrix known in the art. For radiation induced fluorescence detection, the gel matrix includes a known fluorophore, such as Ethidium Bromide.

One end of the capillary column 20 is submerged in a reservoir 40 of running buffer/gel 50. The other end of the capillary column 20 is coupled to the sample vial 60. It is understood that the detection configurations shown in the other embodiments can be equally implemented in a system similar to the CE system 10. Also, the separation channel 30 may be one straight capillary or micro-channel with a section of the detection window closest to the gel-reservoir 40 at the exit end being the detection zone, which is the current preferred mode of our invention. A radiation source 70 (e.g., LED or laser diode) is directly coupled to detection zone 80 outside the walls of the column. A fiber 90 positioned outside the detection zone 80 collects and directs the radiation emissions to a radiation detector 100. Electrodes 110 and 120 are coupled to the sample vial 60 and gel reservoir 40 to complete the electrophoresis path.

For the sake of completeness, it is sufficient to briefly mention the operation of the CE system 10. In operation, a prepared biological sample (e.g., a DNA sample), direct from Polymerase Chain Reaction (PCR) machine is introduced into the far end of the capillary column 20 away from the detection zone 80 by any of a number of ways that is not part of the present invention (e.g., electrokinetic injection from a sample reservoir or physical pressure injection using a syringe pump). The sample binds to the fluorophore.

When a DC potential (e.g., 1–30 KV) is applied between electrodes 110 and 120, the sample migrates under the applied electric potential along the separation channel 30 (e.g., DNA that is negatively charged travels through the sieving gel with an integrated dye matrix/fluorophore toward a positive electrode as shown in FIG. 1) and separates into bands of sample components. The extent of separation and distance moved along the separation channel 30 depends on a number of factors, such as migration mobility of the sample components, the mass and size or length of the sample components, and the separation support medium. The driving forces in the separation channel 30 for the separation of samples could be electrophoretic, pressure, or electro-osmotic flow (EOF) means.

When the sample reaches the detection zone 80, excitation radiation from the radiation source 70 is directed at the detection zone 80. The sample components fluoresce with intensities proportional to the concentrations of the respective sample components (proportional to the amount of fluorescent tag material). The fiber 90 collects and directs the emitted radiation to the detector 100 for detecting the intensities of the emitted fluorescence at a wavelength different from that of the incident radiation. The detected emitted radiation may be analyzed by known methods. For an automated system, a controller 130 controls the operations of the CE system 10.

Multi-Segment Cartridge Based CE Instrument

Figure 2:
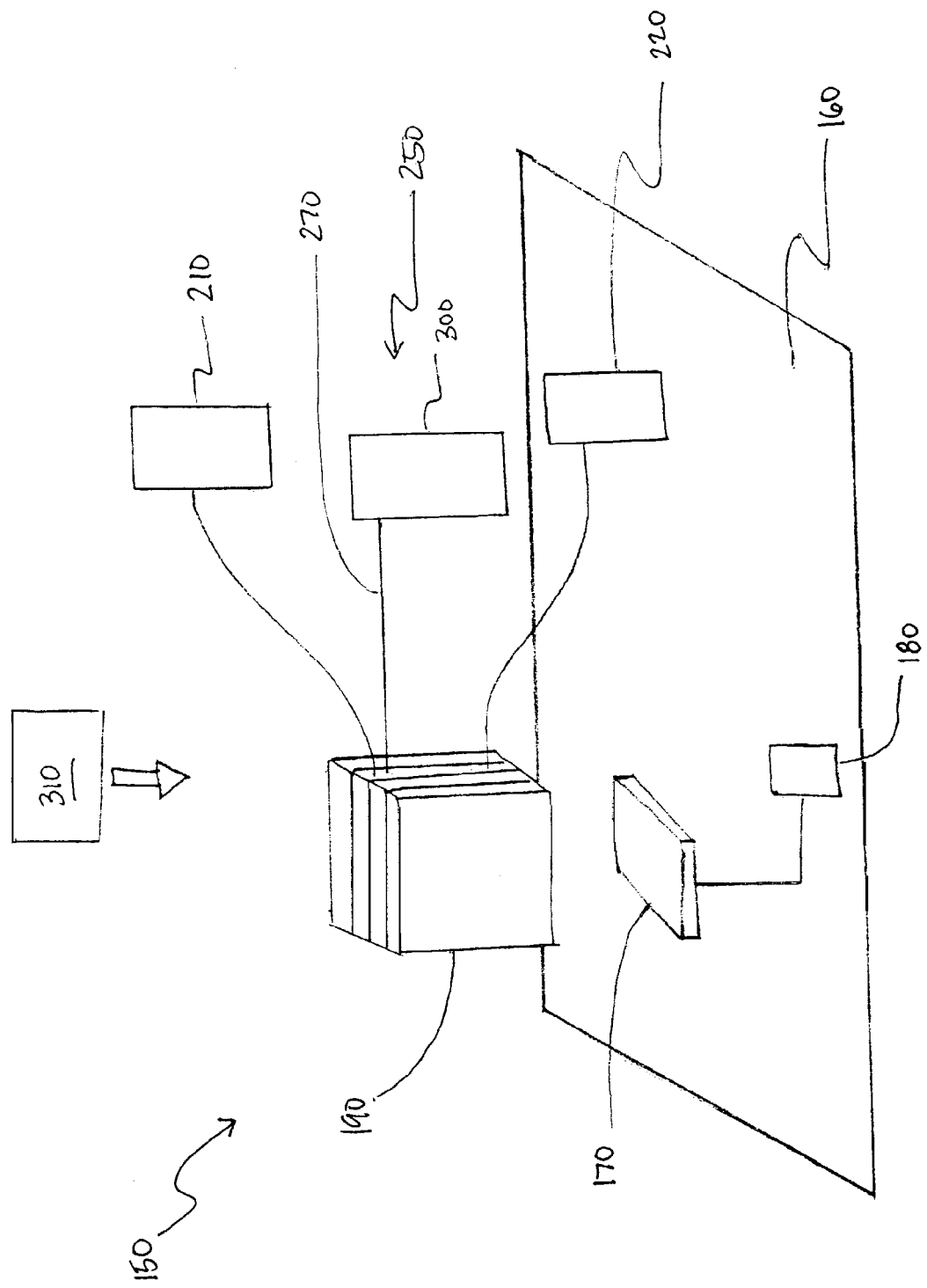
FIG. 2 is a schematic view of a CE instrument in accordance with one embodiment of the present invention.

FIG. 2 shows a schematic view of a CE instrument 150 in accordance with one embodiment of the present invention. The CE instrument 150 includes a base 160, a sample tray 170, a positioner 180, a multi-segment cartridge 190, a pump 210, a voltage source 220, an emission collection system 250, a radiation detector 300, and a controller 310. The base 160 supports the positioner 180, which moves the sample tray 170 in relation to the multi-segment cartridge 190. The positioner 180 can be an X-Z sample handling tray mechanism disclosed in U.S. patent application Ser. No. 10/059, 993. The sample tray 170 holds the samples in preparation for analysis. The sample tray 170 can be a standard PCR 96-well micro-titer plate having 96 wells in an 8×12 grid (8 rows and 12 columns). In some embodiments, the positioner 180 can support and move more than one sample tray 170.

Figure 3:
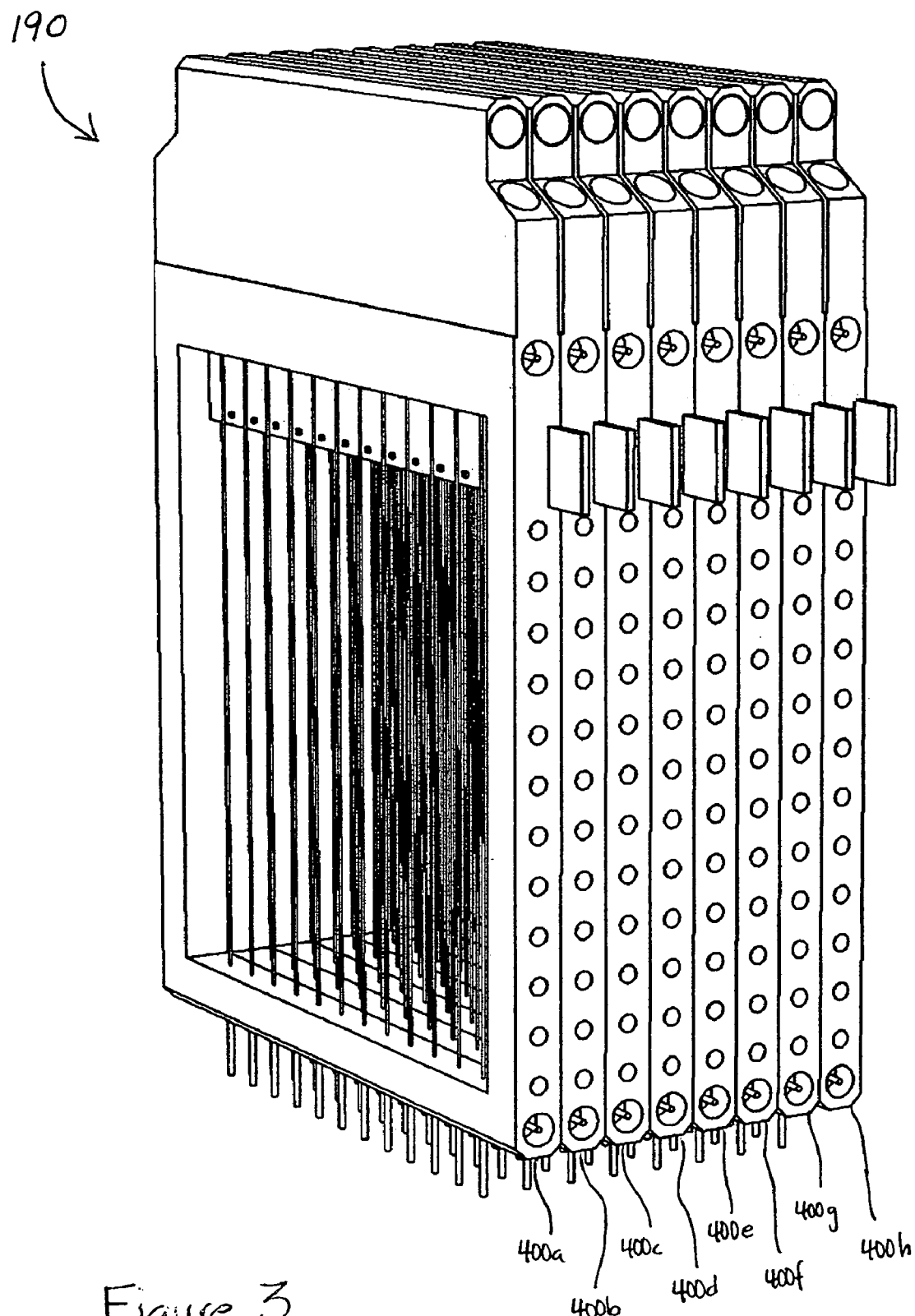
FIG. 3 is a perspective view of the multi-segment cartridge in accordance with one embodiment of the present invention.
Figure 4:
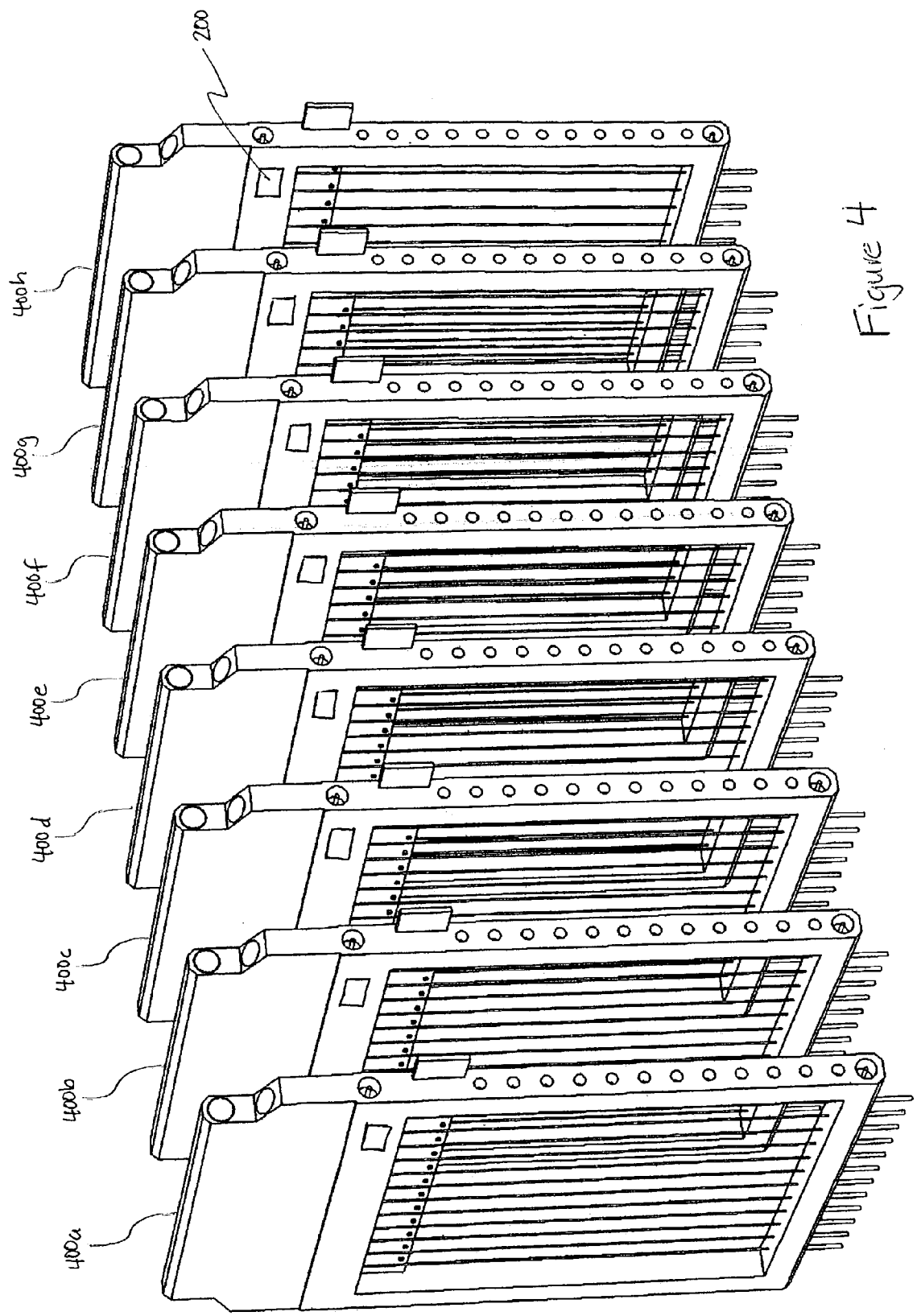
FIG. 4 is an exploded perspective view of the multi-segment cartridge shown in FIG. 3.

The CE instrument 150 includes the multi-segment cartridge 190. The multi-segment cartridge 190 can be supported in the CE instrument 150 by a support bracket (not shown). FIG. 3 is a perspective view of the multi-segment cartridge 190 in accordance with one embodiment of the present invention. The multi-segment cartridge 190 includes one or more multi-channel segments 400 stacked together. In the embodiment shown in FIG. 3, the multi-segment cartridge 190 includes eight modular multi-channel segments 400a–h stacked together. Each of the eight segments 400a–h is designed for use at each of the eight rows of the 96-well micro-titer plate 170. In some embodiments, the segments 400a–h are removeably attached together. Each segment 400 is configured to mate to adjacent segments. A fastener, such as a band encircling the stacked segments (not shown), is used to keep the segments together. In some embodiments, each segment 400 includes a fastener 200 for attaching the segments 400a–h together. FIG. 4 is an exploded perspective view of the multi-segment cartridge 190 shown in FIG. 3. For example, segment 400h includes the fastener 200h for attaching with segment 400g for assembly of the cartridge 190. In some embodiments, the segments 400a–h are not attached to each other, but are stacked in contact with each other. In some embodiments, the segments are positioned and aligned in close proximity to each other by the support bracket (not shown). The CE instrument 150 is capable of supporting a cartridge having one segment or more than eight segments depending upon the particular requirements of the application.

Segment Assembly

Figure 5:
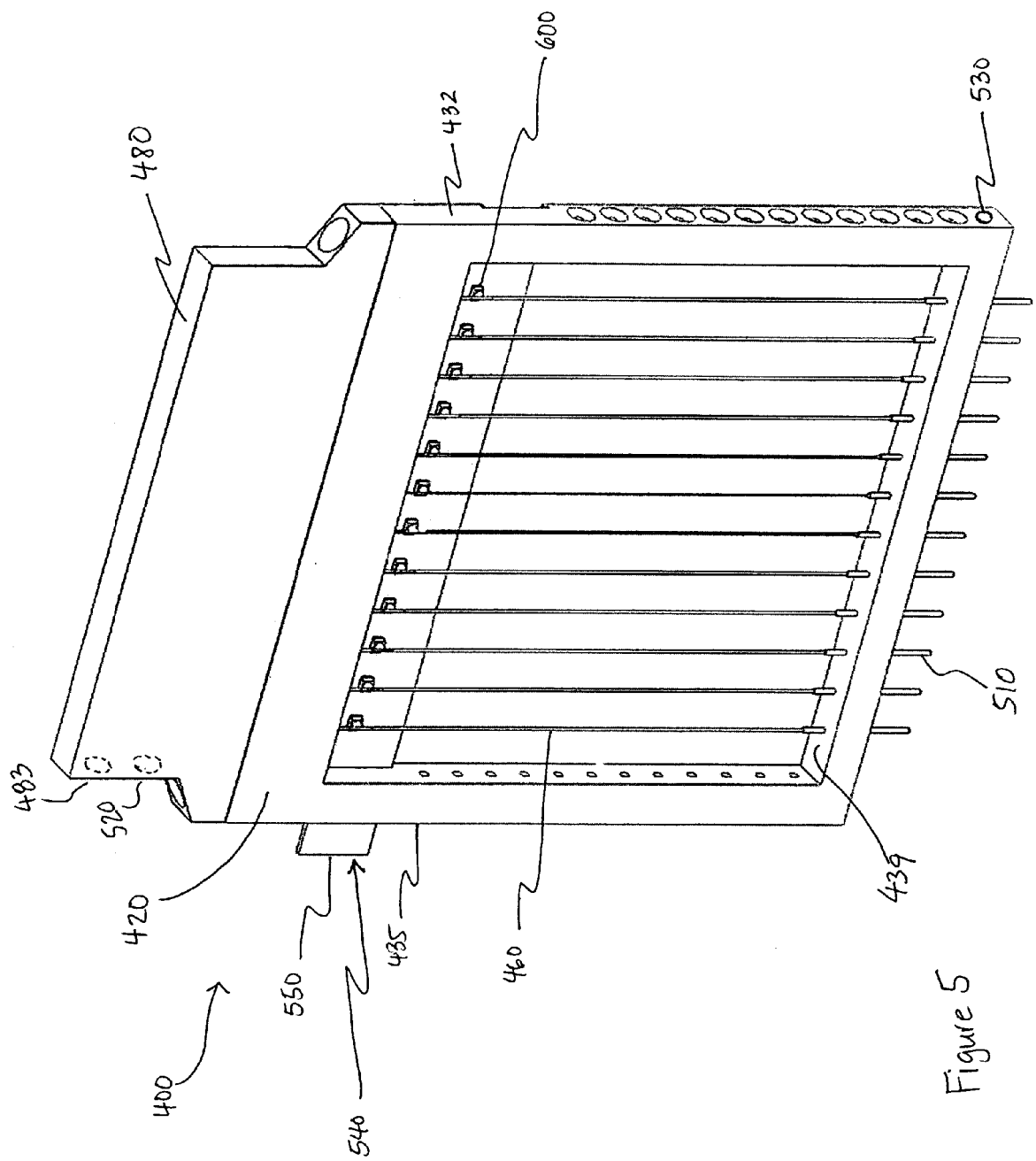
FIG. 5 is a perspective view of the multi-channel segment in accordance with one embodiment of the present invention.

FIG. 5 is a perspective view of the multi-channel segment 400 in accordance with one embodiment of the present invention. The multi-channel segment 400 includes a segment body 420, a plurality of separation channels 460, an integrated buffer reservoir 480, electrodes 500 and 510, and a multi-LED array board 540.

Figure 6:
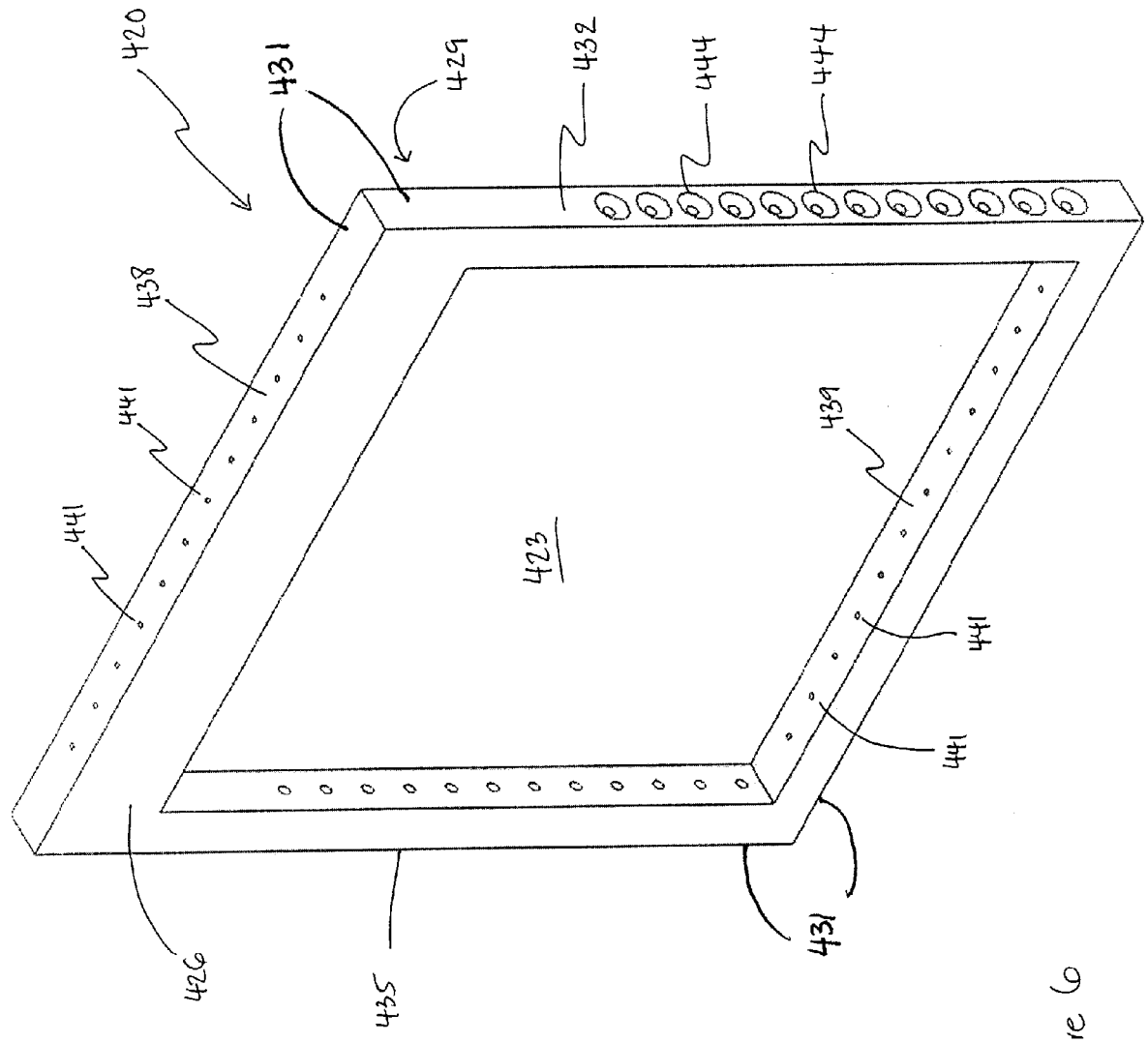
FIG. 6 is a perspective view of the segment body shown in FIG. 5.

The segment body 420 supports the multi-channel capillary array and facilitates direct coupling of the radiation source to the capillary array. FIG. 6 is a perspective view of the segment body shown in FIG. 5. The segment body 420 includes a bay 423, two faces 426 and 429, and a periphery 431, such as sides 432 and 435 and top and bottom ends 438 and 439. The faces 426 and 429 have a larger cross-sectional area than the peripheral sides 432 and 435 (i.e. the periphery has a more slender cross-section than the cross-section of the faces). The top and bottom ends 438 and 439 of the segment body 420 have capillary holes 441 through which the capillaries will be inserted. The multi-channel capillary array is defined in the segment body 420 within the bay 423. The bay 423 can have any shape and configuration that allows positioning of the multi-channel capillary array within the segment body 420. The segment body 420 may be machined, thermoformed, photo-etched or injection molded (e.g., Acrylic, PET, Ultem, Glastic, Fluorosint, or any optically clear plastic). The segment 420 mates with other segments along its faces 426 and 429. Additionally, the radiation source is integrated to the segment body 420 along one of its faces 426 and 429 (as shown in FIG. 5). A plurality of optical fiber connection ports 444 are defined along the periphery, such as sides 432 and 435 of the segment body 420. The ports 444 allow optical fibers to be guided through the sides 432 and 435 to the detection zones of the multi-channel capillary array. The ports 444 facilitate coupling of the optical fibers to the capillary array without interfering with assembly of the multi-segment cartridge 190.

Figure 7:
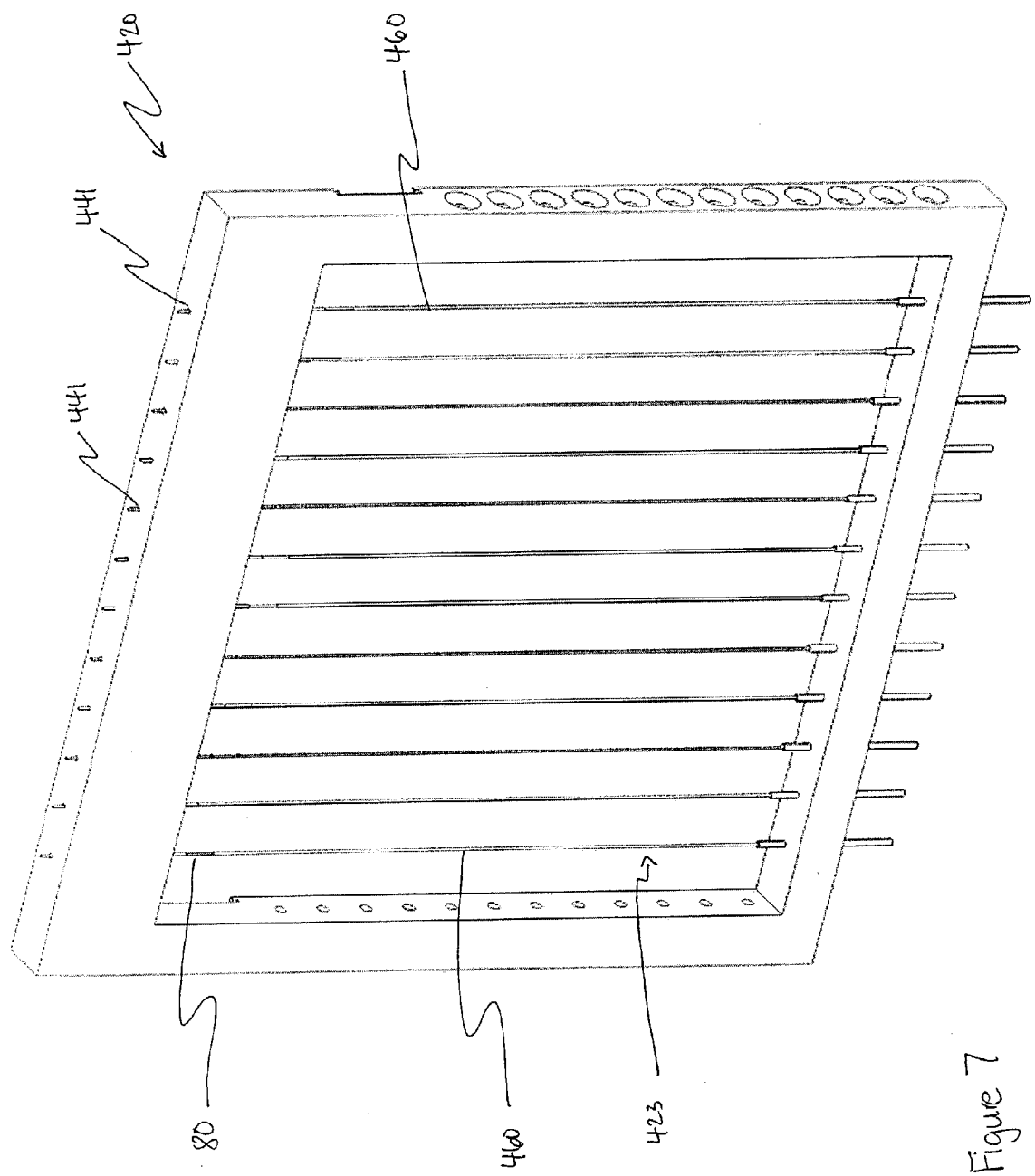
FIG. 7 is a perspective view of the plurality of separation channels integrated within the segment body 420.

FIG. 7 is a perspective view of the plurality of separation channels 460 integrated within the segment body 420. The plurality of separation channels 460 are used for separation and detection of the samples as part of a disposable segment assembly. In the embodiment shown in FIG. 7, the segment body 420 holds up to 12 separation channels 460. However, the segment 400 can support more separation channels depending upon the particular requirements of the application. The 12-channel array 460 includes 12 detection zones 80 defined by micro-channels.

The plurality of separation channels 460 can be a multi-channel fused-silica capillary array. The capillaries 460 can be coated with polyimide, with a section of the polyimide coating removed to provide a detection window 80. The capillaries 460 are placed through the capillary holes 441 until they reach the lower end of the segment body 420 with the cathode tips. Staples may be used to secure the capillaries 460 to the segment body 420. The segment body 420 supports the capillary array 460 such that the detection zones 80 are positioned within the bay 423. When the 12-channel segment 400 is assembled with seven other segments, the 8-segment cartridge supports 96 capillaries in an 8×12 grid.

Referring back to FIG. 5, the segment 400 is integrated with the top buffer reservoir 480 common to all capillaries 460 in the segment body 420. The buffer reservoir 480 is a chamber that can be attached to the segment body 420 with an O-ring as a seal or hermetically laser welded or sonic welded. The gel reservoir 480 may have transparent, or clear, windows on each side for inspection of the gel level. The reservoir 480 containing the gel is sealed, such as hermetically sealed at the segment body 420, which allows the segment 400 to be handled by holding it in any orientation without leakage of the gel. (There is negligible leakage or exposure at the capillary tips because of surface tension and high viscosity within the micro-bore of the capillaries.) The reservoir 480 has a rubber septum 483 that is pierced by an instrument-mounted needle (or any sharp object) that provides air pressure from a pump or compressed air tank. This allows air pressure to fill the capillaries 460 with the gel/buffer solution after each separation run, and to purge the old gel from the previous run in the process. This approach assures the proper containment of the gel inside the reservoir 480; and it also provides a simple and reliable means of accessing the gel reservoir and of providing enough air pressure to effect a purging flow of gel through the capillaries 460 prior to applying high voltage to effect CE separation. The septum 483 is disposed along sides 432 and 435 of the segment 400, which facilitates connection of the air pressure to the reservoir 480 without interfering with assembly of the multi-segment cartridge 190.

Referring to FIG. 2, the gel reservoir 480 is coupled to a modular air pressure pump or compressed air tank 210 when integrated in the CE instrument 150. The pump/tank 210 provides the required air pressure to force gel through the capillaries 460. Depending on the viscosity of the gel, pressures of up to 40 PSI have been applied to the capillaries 460 through the gel-filled reservoir 480.

Figure 8:
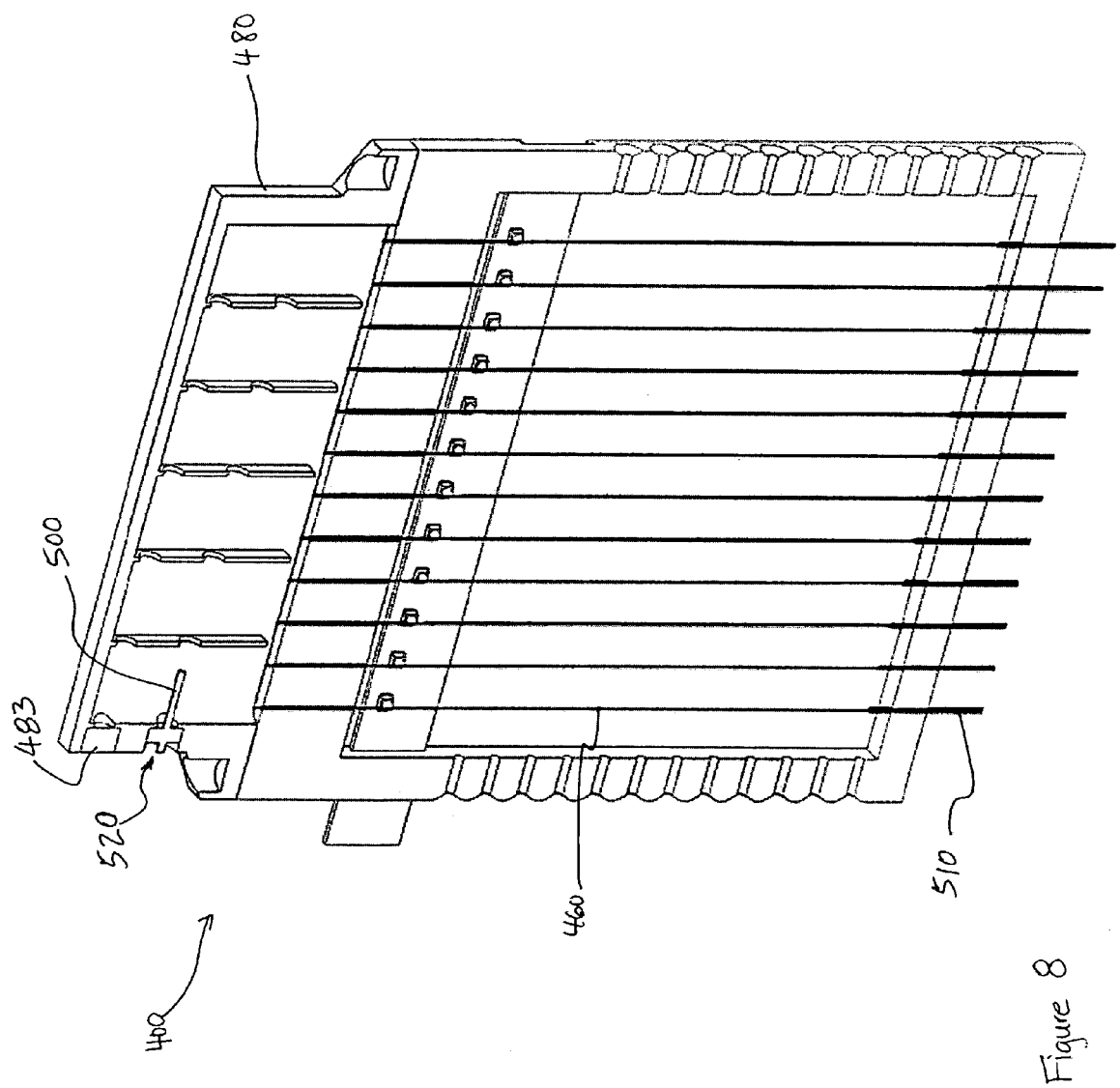
FIG. 8 is a cross sectional view of the segment 400 shown in FIG. 5.

Each segment 400 has a single electrode (anode) at the buffer reservoir 480 and multiple electrodes (cathodes) at the lower end 439 the segment body 420 as part of the segment 400 assembly. FIG. 8 is a cross sectional view of the segment 400 shown in FIG. 5. The gel reservoir 480 is equipped with a built-in electrode (anode) 500 common for all capillaries 460 in the segment 400 and a cathode tip 510, positioned at the lower end 439 of the body 420, for each capillary 460. The electrodes 500 and 510 are automatically connected to a high voltage power supply 220 (or power supplies; i.e. 8-HV power supplies for each of the individual segments) via off the shelf pogo-pins when installed inside the instrument 150. A commercially available high voltage power supply (e.g., Emco) can be used to deliver 0 to 20 KV of electrical field to gel-filled capillaries 460 for the electrokinetic injection and separations of sample fragments (the individual HV power supplies could deliver HV power on demand to each of the segments. The HV power supplies could be modular and low-cost, which provides HV power by delivering low voltages, i.e. up to 5–10 KV, to each of the segments). Referring to FIG. 5, the segment 400 includes an anode connector 520 and a cathode connector 530 disposed along the periphery 431, such as the side 432, of the segment body 420. The anode connector 520 provides connection of the anode 500 to the power supply 220 (individual power supplies), and the cathode connector 530 provides connection of the multiple cathodes 510 to the power supply 220. Providing the anode and cathode connectors 520 and 530 along the periphery 431 of the body 420 allows connection of the electrodes 520 and 530 to the power supply 220 without interfering with assembly of the multi-segment cartridge 190.

Figure 9:
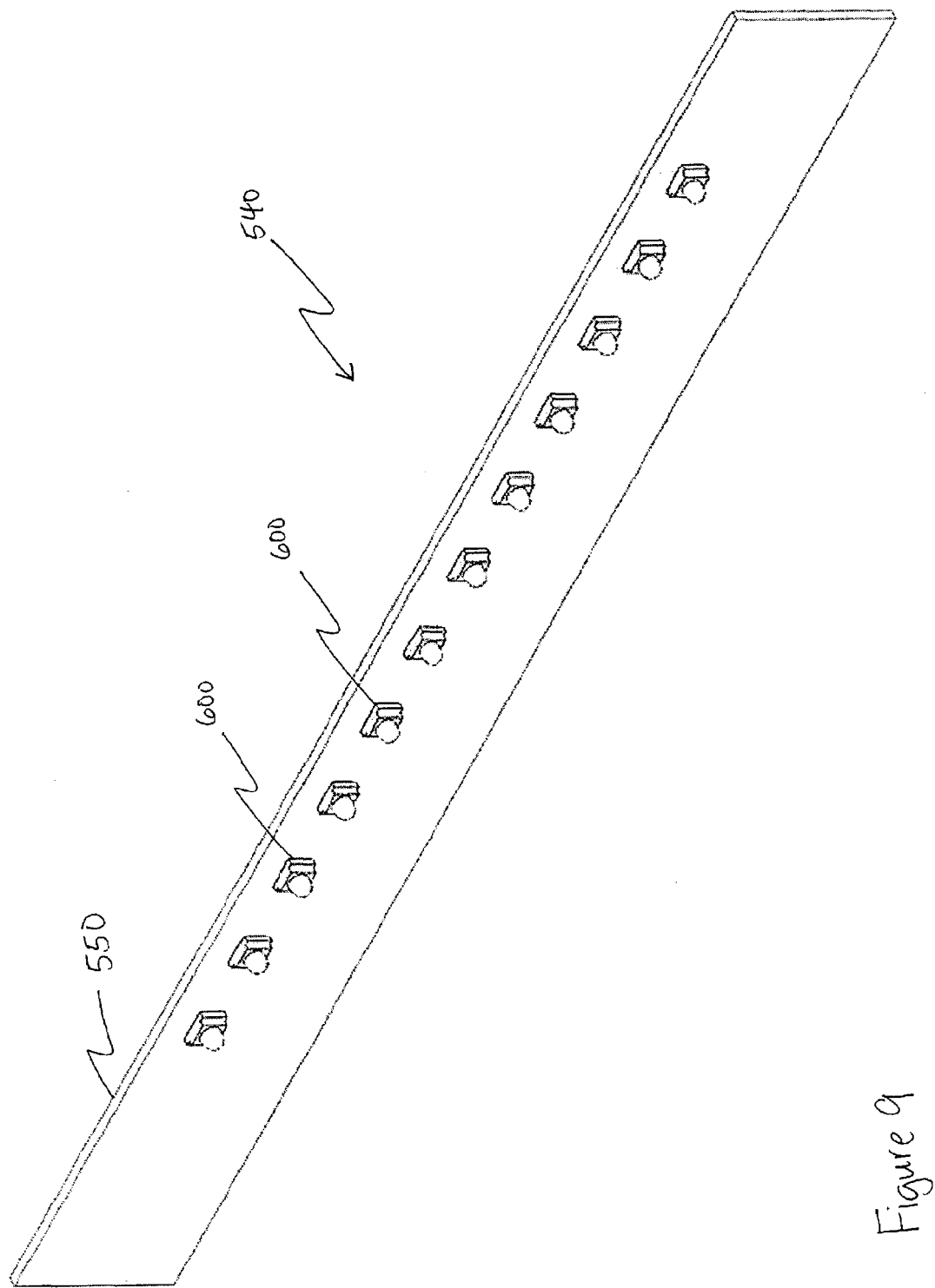
FIG. 9 is a perspective view of the multi-LED array board in accordance with one embodiment of the present invention.

As shown in FIG. 5, each segment 400 includes an integrated multi-LED array board 540 for providing a radiation source. FIG. 9 is a perspective view of the multi-LED array board 540 in accordance with one embodiment of the present invention. The multi-LED array board 540 includes a printed circuit board (PCB) 550 supporting an array of surface mount type (SMT) LED's 600. The PCB 550 provides a structural base for supporting the multi-LED array 600, and provides the necessary electrical connections to each SMT LED 600.

In the embodiment shown in FIG. 9, the PCB 550 supports 12 super bright SMT LED's 600. The SMT LED's 600 may be super bright blue or green LED's (e.g., Nichia P/N: NSSG440TVR or GELcore P/N: GEGMSM030-CB). The attractive features of LED's as light sources are their low cost, small size, long lifetime, good intensity and stability resulting in low noise, and the possibility of direct electronic modulation of the intensity. Since the response time of these LED's is very high (at a few hundred nanoseconds), they can be pulsed at greater forward currents, up to 100 mA in pulsed mode operation, to obtain high radiant peaks. Pulsed operation of LED's can typically be achieved by the transistor drive circuits. Significantly higher peak LED light output can be realized from large drive current pulses at low duty cycles (i.e., 5%, 10%, 25% or 50%) than DC operation. Different color LED's (i.e., blue or green LED's) could be used as radiation sources for excitation of different fluorophores (different applications). The multi-LED array board 540 could be designed to be wavelength specific, or for two different wavelength LED's (e.g., at 530 nm and 470 nm) for dual wavelength detection. Reference is made to U.S. patent application Ser. No. 10/277,961, entitled "Multi-color Multiplexed Analysis in a Bio-Separation System," filed on Oct. 21, 2002, which is commonly assigned to BioCal Technology, Inc., the assignee of the present invention, and which is fully incorporated by reference herein. Alternative excitation light sources, which can be directly coupled to the capillary array 460, can be employed as well.

Figure 10:
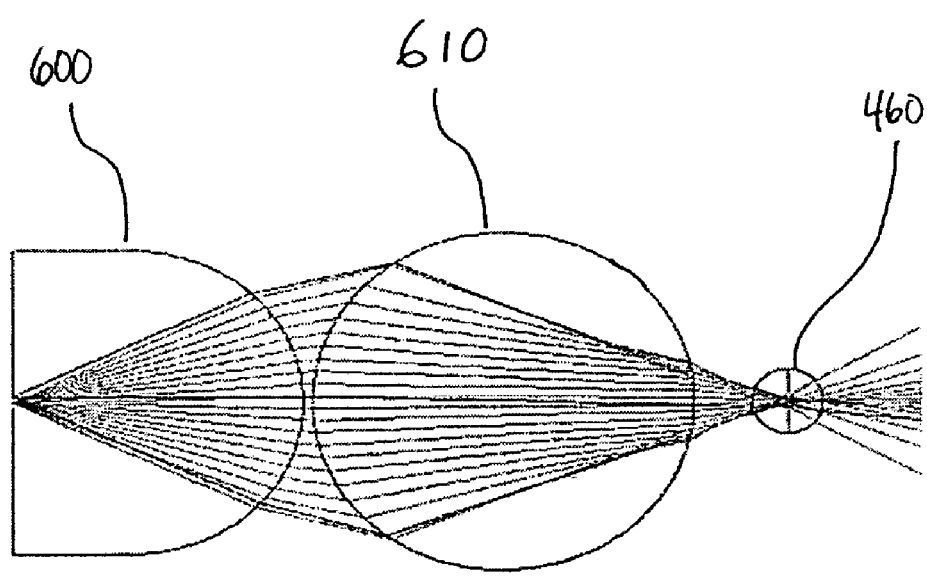
FIG. 10 shows an SMT LED directly coupled to a capillary.

Referring to FIG. 5, the PCB 550 can be integrated with the cartridge along on either faces 426 and 429 of the segment body 420. When integrated with the segment body 420 (as shown in FIG. 5), the multi-LED array 600 is directly coupled to the multi-capillary array 460. FIG. 10 shows an SMT LED 600 directly coupled to a capillary 460. A relay lens 610 (e.g., a Sapphire micro-ball lens) can be used to direct excitation light from the SMT LED 600 to the capillary 460. The multi-LED array board 540 can include an array of relay lenses 610 for direct coupling of the array of LED's 600 to the array of capillaries 460.

The design of the segments 400 allows excitation light to be directly coupled to the multi-capillary array 460 even when the segments 400 are stacked together. As shown in FIG. 3, the multi-LED array board 540 does not interfere with assembly of the multi-segment cartridge 190. The multi-LED array board 540 can be removeably attached to the segment body 420, allowing integration of the multi-LED array board 540 with any of the segments 400 in the cartridge 190 and allowing the multi-LED array board 540 to be recycled when the segment 400 has been discarded. Alternatively, the segment 400 can be manufactured with the multi-LED array board 540 fixedly attached to the segment body 420. The multi-LED array board 540 and the segment 400 can be discarded when the buffer reservoir 480 is depleted.

It is further noted that the detection zone 80 is not necessarily a well-defined zone with well-defined boundaries, due to the nature of the substance, the incident radiation, and the fluorescence emissions. It is generally a zone in which light from the SMT LED's 600 is directed to cause fluorescence emissions and the detection optics is aimed to capture part of such fluorescence emissions. Light from the SMT LED's 600 may cause fluorescence emissions outside the detection zone, and some of the emissions from within the zone may not be detected by the detection optics. The closer the SMT LED 600 is to the detection zone or the higher the power density of excitation light, the stronger the collected emission signals are.

Figure 11:
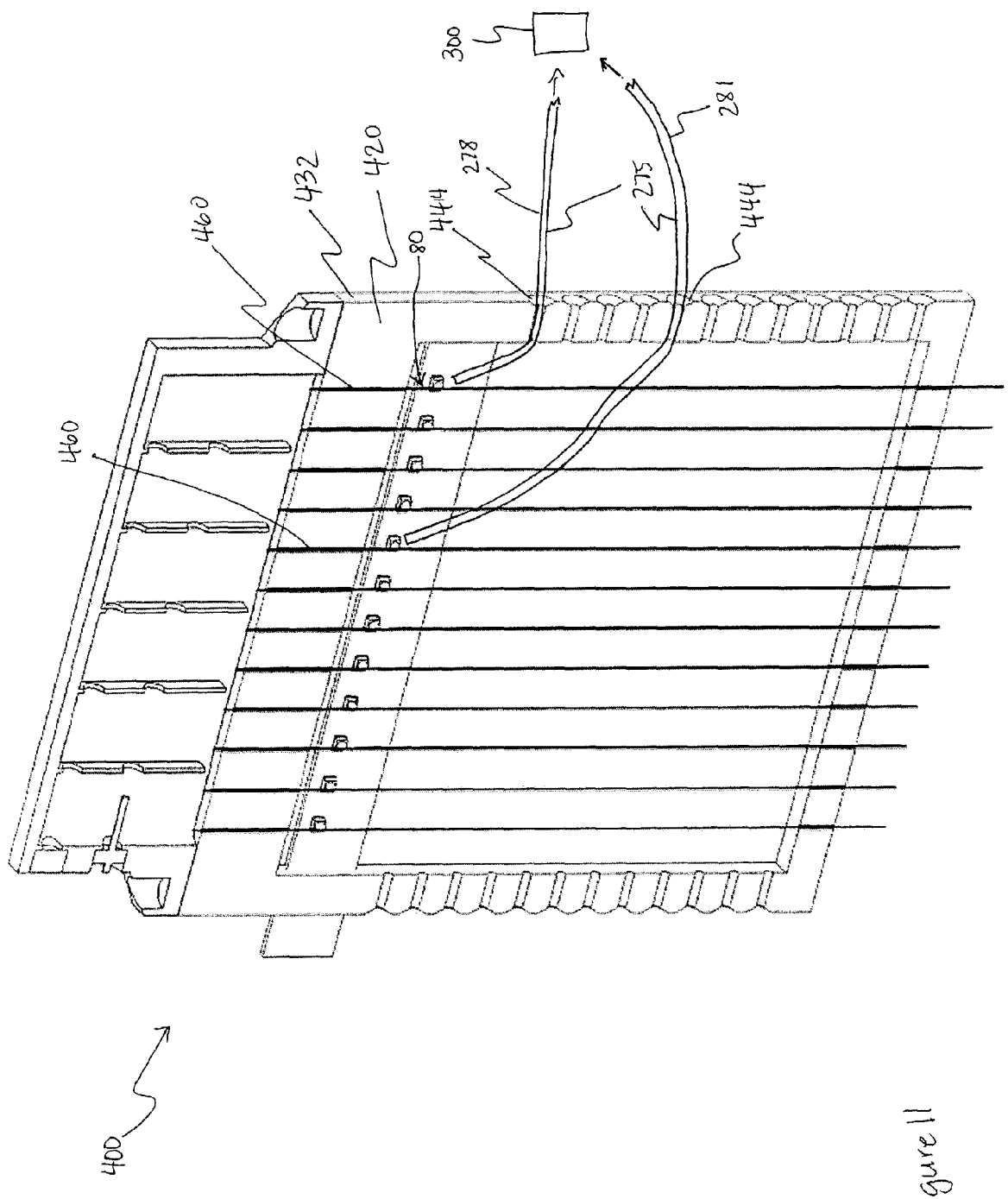
FIG. 11 is a cross-sectional view of the segment showing a detection fiber array integrated into the segment body.

Referring to FIG. 2, the instrument 150 includes the emission collection system 250 having a detection fiber bundle 270 and a radiation detector 300. FIG. 11 is a cross-sectional view of the segment 400 showing a detection fiber array 275 integrated into the segment body 420. FIG. 11 shows two example fibers 278 and 281 integrated into the segment 400. The detection fiber array 275 is comprised of a plurality of detection fibers, such as fibers 278 and 281. The detection fibers can be a large core optical fiber (220 µm O.D., 0.22 NA fibers, but could also be in ranges of: 100–1000 µm O.D., 0.12–0.5 NA). One end of a detection fiber 278 is inserted through the fiber connection port 444 along the periphery 431, such as the side 432, of the segment body 420 and guided to a capillary 460, where the end of the detection fiber 278 is positioned and aligned with the detection window 80. The end of the detection fiber 278 is positioned orthogonal and at 90 degrees with respect to the axis of the excitation light. Each of the capillaries 460 has a detection fiber coupled to it. By inserting the fibers 275 along the periphery 431 of the segment body 420, the fiber array 275 does not interfere with assembly of the multi-segment cartridge 190.

Referring to FIG. 2, the detection fibers 275 from all the segments 400a–h may be bundled together at the other end to form the fiber bundle 270. The fiber bundle 270 is coupled to the radiation detector 300. The radiation detector 300 can be one or more photo-multiplier tubes (PMT) (e.g., R5984 Hamamatsu PMT). The fiber bundle 270 collects the emission signals originating from the capillary array 460 and relays the signals into the PMT 300 where the signals are filtered by single or multiple emission filters (not shown) and are read in time-staggered multiplexed scheme. A time-staggered multiplexed detection scheme is disclosed in U.S. patent application Ser. No. 10/060,052, entitled "Optical Detection in A Multi-Channel Bio-Separation System," filed on Jan. 28, 2002, which is assigned to BioCal Technology, Inc., the assignee of the present invention, and which is fully incorporated by reference herein. The sampling frequency for each capillary 460 can be 10–100 Hz.

The collection system 250 can support dual-wavelength collection. In some embodiments, a single detection fiber can be utilized for collecting the dual-wavelength signal and then passing the signal to a filter where the wavelengths are separated for reading. In some embodiments, two detection fibers can be coupled to one capillary, one fiber for each of the two wavelengths.

The multi-segment cartridge can include front and rear covers (not shown). The front and rear covers are placed on the segments at the outer ends of the cartridge. The front and rear covers can have vent holes through which cooled air flows inside the cartridge to cool the capillaries. Additionally, the covers can facilitate fastening the segments together.

Figure 12:
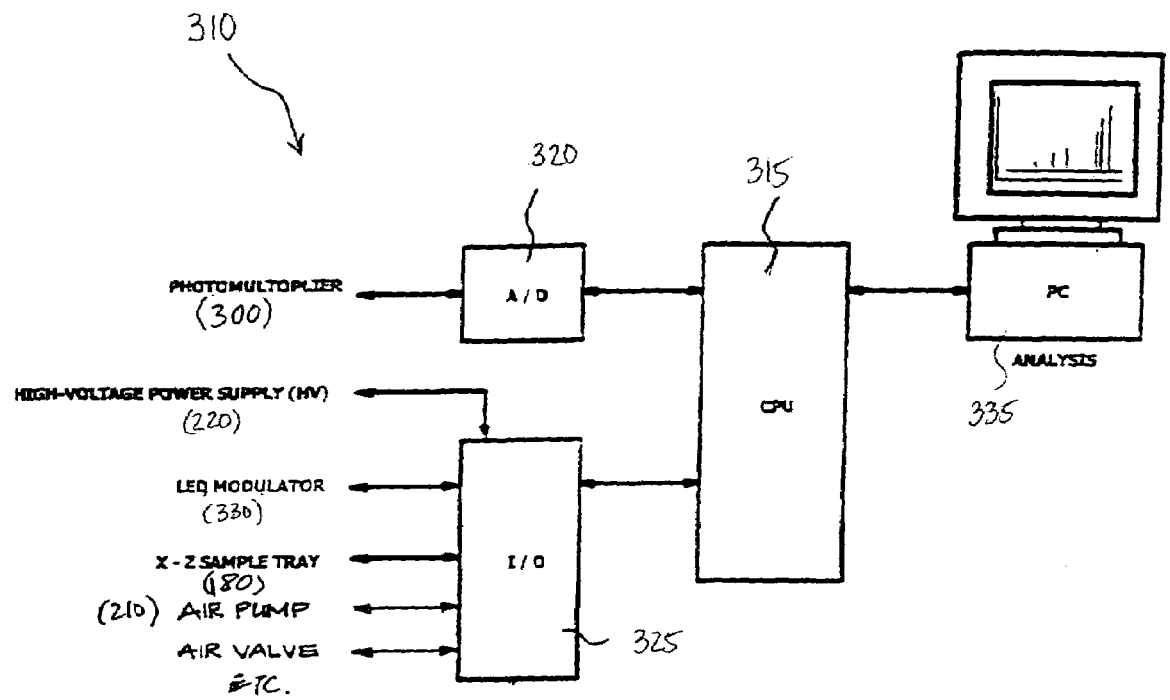
FIG. 12 is a block diagram of the controller in accordance with one embodiment of the present invention.

Referring again to FIG. 2, the instrument includes the controller 310. In accordance with one embodiment of the present invention, a block diagram of the controller 310 for the instrument 150 is shown in FIG. 12. The controller 310 includes a CPU 315, an A/D converter 320 for converting detection signals from the PMT 300 (shown in FIG. 2) to corresponding digital signals, and an I/O interface 325 for transferring and receiving signals to and from respective parts of the instrument 150 by instructions from the CPU 315. The I/O interface 325 also controls the high-voltage power supply 220 for sample injection and electrophoresis functions of the instrument 150, a circuit for modulating the LED's 330, sensors, air pump 210, air valve, and motors for the positioner 180. The CPU 315 may be further coupled to an external personal computer 335, which in turn performs data processing or additional control function for the instrument 150. The CPU 315 and/or the PC 335 may be programmed with control functions dictated by LabVIEW™ software available from National Instruments Corporation, or any other developed software (developed by BioCal) to control various features and functions of the instrument 150.

The components of the controller 310, with the exception of the PC 335, may be packaged as an electronic board on instrument and electrically coupled to the PC 335 via a serial port (not shown), or they may be part of a separate controller module outside of the instrument 150. The CPU 315 and/or the PC 335 are programmed to accomplish the various control functions and features for the instrument 150. In one embodiment, the PC can be configured to provide the front panel control (i.e., user interface) for the instrument, and the board may be configured to provided the time staggered/time multiplex detection controls. It would be within a person skilled in the art to implement the program code given the functions and features disclosed herein. An A/C power filter/switch is provided for the instrument.

Operation of Instrument

In operation, the positioner 180, with the sample tray 170, is used to present the amplified DNA samples (or analytes) to each micro-bore separation channels 460. The positioner 180 aligns wells of the tray 170 under the rows of capillary tips 460 and dips the tips into the wells or lifts the tray 170 up to the capillary tips 460. By applying a voltage, electro-kinetic injection moves a known amount of the DNA sample to the beginning of the separation columns. After injection, the DNA samples from the sample tray 170 may be replaced with a running buffer from another tray. By applying high voltage across the total length of the capillary separation channels, separation of the DNA sample into DNA fragments is achieved. Up to 1000 V/cm (typically 300 V/cm) of high voltage is applied, which provides fast separations of less than 10 minutes along the entire length of the separation channel. The total separation length is about 12.5 cm up to the detection zone. The separation capillary length is about 16.0 cm. High voltage is applied from the bottom to the top of one single capillary with 75 micron I.D. During electrophoresis, the rate at which the DNA fragments move through the sieving gel is inversely proportional to their mass; i.e., lighter (or smaller) DNA fragments move more quickly than heavier (or larger) ones. As the fragments approach the end of the separation channel and enter into the detection zone, the excitation light energy from each of the SMT LED's 600 is delivered by the relay lenses 610 from outside the detection window 80, illuminating the migrating DNA fragments with the attached intercalating dye from the sample tray 170. As the DNA fragments move through the sieving gel, or linear polymer solution (e.g., 25 mM Mops-Tris pH 7.55, as referenced in "Pace Setter", Vol. 3, Issue 1, April 1999), a DNA intercalating dye (Ethidium Bromide) within the sieving gel allows the migrating DNA fragments to be detected. Experiments have shown that detection sensitivities of 100 ng/ml (0.02 ng of the HaeIII digest φX174 DNA test mix) are achievable, which is several orders of magnitude better than conventional slab gel electrophoresis devices using the same intercalating dye. As the SMT LED's 600 are time-multiplexed (with sampling frequency of 10–100 Hz), 96 emission signals coupled to 96 emission detection fibers 275 will reach the single PMT 300 (or multiple PMT's) in a time-staggered manner by a single fiber bundle 270.

To prepare for the next run with a different sample, the old gel from the previous run is purged from the capillaries 460 by pressuring the reservoirs 480 to refill the capillaries 460 with fresh gel. The tips of the capillaries may be cleaned with water or a cleaning solution. When the capillaries 460 are refilled and ready for the next run, the tips of the capillaries are dipped into the samples by repositioning the tray 170. The above-mentioned sequence of process may be programmed as one of the automated functions of the controller 310.

It is noted that because the sample analytes that flowed to the gel reservoir at the exits of the capillaries are in such small amount and volume concentration compared to the volume of the reservoir, and that the analytes are expected to be mixed within the gel reservoir, there will only be a negligible trace of analytes from past runs in the reservoir, and that will be evenly distributed in the gel that refills the capillaries for the next run. Any noise from this negligible trace would be relatively small background noise that can be easily removed from the detected signal in the data analysis.

A person skilled in the art will recognize that the instrument incorporating the essence of this invention can also be used for other bimolecular analysis. For example, by altering the separation gel or buffer, the instrument can also be modified to analyze biomolecules like proteins, carbohydrates, and lipids. Using a number of multi-channel segments of the present invention having different buffer/gel chemistries, capillaries, etc., particular buffer/gel chemistry, with matching capillary (e.g., with particular internal wall coatings and column sizes), may be easily interchanged to suit the particular sample based separation applications and run conditions, to achieve different separations, types, speeds, resolutions, etc. A particular segment may be set aside, and later reused for conducting future separation runs. Compared to the prior art CE instruments, the set up time to prepare the present CE instrument using the multi-segment cartridge to run different test can be reduced significantly, since the separation columns, the separation medium, and at least the detection optics requiring fine alignment with respect to the capillaries are all self contained within the segments. The reusability of the segments significantly reduces the material cost for the CE instrument. Also since the gel matrix with intercalated dye is hermetically sealed inside segment it provides a good solution for an environmentally safe/"Green" product. The fluorophore and/or gel matrix may contain carcinogens and other materials harmful to health and environment. By packaging the gel inside the segment, it significantly eases handling and improves safety. The segments may be collected and disposed of accordingly in an environmentally safe manner, or it can be recyclable, with spent parts replaced or refurbished by trained technicians to avoid harm to the environment.

With this automated and modular with integrated optics and self-aligning (non-moving micro-optical parts) multi-channel approach, the operation of the instrument becomes simpler, more reliable yet provides high throughput. The cartridge with self-contained, pre-aligned optics with respect to the separation channels, can be easily snapped into the CE instrument. Further, this multi-channel detection scheme could be expanded or scaled up to more than 96 detection channels without impairing the detection sensitivity. The other advantage of this simple time-multiplexed type detection method is that there is negligible or no cross talk between the channels compared with any other high-throughput LIF detection schemes.

While in the embodiments described above, the multiple radiation sources are at the same wavelength, it is within the scope and spirit of the present invention to configure the multiple radiation sources at different wavelengths, to complement the specific samples, sample based detection applications or gel chemistries in the different capillaries.

Radiation emissions from the detection zone may be output axially along the separation medium. A widened detection zone may be adopted. References are made to U.S. patent application Ser. No. 09/887,871 entitled Optical Detection in Bio-Separation Device Using Axial Radiation Input, U.S. patent application Ser. No. 09/887,953 entitled Optical Detection in Bio-Separation Device Using Axial Radiation Output, and U.S. patent application Ser. No. 09/887,872 entitled Optical Detection in Bio-Separation Device Using a Widened Detection Zone, all filed on Jun. 22, 2001, which are commonly assigned to BioCal Technology, Inc., the assignee of the present invention, and which are fully incorporated by reference herein.

The low cost instrument of the present invention has a disposable/recyclable multi-channel, multi-segment cartridge design (since, most of the cartridge body parts could be retrieved and then repackaged or reused. The only part that would be replaced are the capillaries and the gel), a fluorescence detection system, and a built-in sample handling tray (96-well plate) mechanism. Experiments have demonstrated the analyses of samples are completed in just 4 to 10 minutes per 96-channel (96 parallel results for 96 test samples). The DNA analyzing instrument is an all-in-one high throughput workstation that handles complete DNA fragment analysis from injection to detection to fragment data collection. Detection sensitivity for a single capillary using the described detection mode of the present invention is in the order of 0.02 ng of the DNA fragment in less than 10 minutes of separations (using HaeIII digest φX174 bacteriophage DNA test mix). This kind of approach for having 96 micro-channels/capillaries running in parallel produces results within 10 minutes for all 96 electrophoresed samples. This kind of separation speed and detection sensitivity is several orders of magnitude better than conventional slab gel-electrophoresis techniques and 96-capillary CE techniques.

While the invention has been particularly shown and described with reference to the preferred embodiments, it will be understood by those skilled in the art that various changes in form and detail may be made without departing from the spirit, scope, and teaching of the invention. A person skilled in the art will recognize that the instrument incorporating the essence of this invention can also be used for bimolecular analysis other than DNA analysis. For example, by altering the separation gel or buffer, the instrument can also be modified to analyze biomolecules like proteins, carbohydrates, and lipids.

By way of example and not limitation, the detection scheme of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions, including other types of emissive radiation, such as phosphorescence, luminescence and chemiluminescence, as well as absorbance based detection.

Furthermore, while the separation channels in the described embodiments are defined by cylindrical columns or tubes, it is understood that the concepts of the present invention is equally applicable to separation channels defined by open channels, for example micro-channels defined by etching in a substrate (micro-fluidics type devices or bio-chips).

The transport mechanism can be configured to move the trays in a horizontal plane, and an additional transport mechanism may be provided to move the cartridge vertically to access the trays.

Accordingly, the disclosed invention is to be considered merely as illustrative and limited in scope only as specified in the appended claims.

We claim:

1. A multi-channel segment for bio-separation, comprising:
   a body having a face and a side;
   a plurality of separation channels for analytes defined in the body, each defining a detection zone;
   a chamber in the body defining a reservoir in fluid communication common with the plurality of separation channels, the chamber containing a separation support medium;
   a radiation source attached along the face of the body wherein the radiation source comprises an array of LED's directly coupled to the detection zones; and
   radiation collection optics aligned with respect to the detection zone through the side of the body.

2. The multi-channel segment of claim 1, characterized by at least one of the following: portable, reusable, modular and interchangeable with other segments having different one of separation support medium and separation channels.

3. The multi-channel segment of claim 1, further comprising a first electrode electrically coupled to the reservoir.

4. The multi-channel segment of claim 3, further comprising a second electrode electrically coupled to each end of the plurality of separation channels that is away from the reservoir.

5. The multi-channel segment of claim 4, further comprising a connector disposed substantially about the side of the body, and electrically coupled to the first and second electrodes for connection to an external voltage source.

6. The multi-channel segment of claim 1, wherein the radiation collection optics comprise optic fibers guided through the side of the body, each having an end aligned with the detection zone.

7. The multi-channel segment of claim 1, wherein the radiation source is removeably attached along the face of the body.

8. The multi-channel segment of claim 1, wherein the radiation source is directly coupled to the detection zone through a lens element.

9. The multi-channel segment of claim 1, wherein the radiation source further comprises a PCB attached along the face of the body for supporting the array of LED's.

10. The multi-channel segment of claim 1, wherein the separation channels comprise capillary columns supported in the body.

11. The multi-channel segment of claim 1, wherein the separation support medium comprises a gel.

12. The multi-channel segment of claim 11, wherein the gel is of a type suitable for capillary electrophoresis.

13. The multi-channel segment of claim 1, further comprising a septum disposed substantially about the side of the body for introducing pressurized air into the reservoir to purge and fill the separation channels with the separation support medium.

14. A multi-segment cartridge for bio-separation comprising a plurality of multi-channel segments attached to each other, each segment comprising:
   a body having a face and a side;
   a plurality of separation channels for analytes defined in the body, each defining a detection zone;
   a chamber in the body defining a reservoir in fluid communication common with the plurality of separation channels, the chamber containing a separation support medium;
   a radiation source attached along the face of the body such that the radiation source is directly coupled to the detection zones and does not interfere with an adjacent attaching segment; when the segments are attached together and
   radiation collection optics aligned with respect to the detection zone through the side of the body.

15. The multi-segment cartridge of claim 14, wherein the plurality of multi-channel segments are attached to each other at their faces.

16. The multi-segment cartridge of claim 15, further comprising a fastener for securing the plurality of multi-channel segments together.

17. The multi-segment cartridge of claim 14, wherein each segment comprises a first electrode electrically coupled to the reservoir, and a second electrode electrically coupled to each end of the plurality of separation channels that is away from the reservoir.

18. The multi-segment cartridge of claim 17, wherein each segment comprises a connection disposed substantially about the side of the body, and electrically coupled to the first and second electrodes for connection to an external voltage source.

19. The multi-segment cartridge of claim 14, wherein each segment comprises a septum disposed substantially about the side of the body for introducing pressurized air into the reservoir to purge and fill the separation channels with the separation support medium.

20. A bio-separation instrument, comprising:
   a base;
   one or more multi-channel segments stacked together, wherein each Segment comprises:
      a body having a face and a side;
      a plurality of separation channels for analytes defined in the body, each defining a detection zone;
      a chamber in the body defining a reservoir in fluid communication common with the plurality of separation channels, the chamber containing a separation support medium;
      a radiation source attached along the face of the body such that the radiation source is directly coupled to the detection zone and does not interfere with an adjacent attaching segment when the segments are stacked together;

radiation collection optics aligned with respect to the detection zones through the side of the body;

a septum disposed substantially about the side of the body for introducing pressurized air into the reservoir to purge and fill the separation channels wit the separation support medium;

positioning means supported on the base for positioning samples with respect to the separation channels and in fluid communication with the separation channels;

separation means for effecting bio-separation of the samples along the separation channels; and control means for controlling operations of the bio-separation instrument.

21. The bio-separation instrument of claim 20, wherein the separation means comprises electrophoretic means for effecting electrophoresis separation of the samples in the separation channels.

22. The bio-separation instrument of claim 21, wherein the electrophoretic means comprises each segment including a first electrode electrically coupled to the reservoir, a second electrode electrically coupled to each cud of the plurality of separation channels that is away from the reservoir, a voltage source, and a connector disposed substantially about the side of the segment and electrically coupled to the first and second electrodes for connection to the voltage source.

23. The bio-separation instrument of claim 20, further comprising pressure means connected to the septum of each segment for pressurizing the reservoir to purge and fill the separation channels.

24. The bio-separation instrument of claim 20, further comprising a radiation detector coupled to the radiation collection optics capable of reading emissions passed from the radiation collection optics in a time-staggered multiplexed scheme.

* * * * *